(12) United States Patent
Bonner et al.

(10) Patent No.: US 10,350,416 B2
(45) Date of Patent: Jul. 16, 2019

(54) INTRACARDIAC PACEMAKER WITH SENSING EXTENSION IN PULMONARY ARTERY

(71) Applicant: Medtronic, Inc., Minneapolis, MN (US)

(72) Inventors: Matthew D Bonner, Plymouth, MN (US); Mark K Erickson, Brooklyn Park, MN (US); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 170 days.

(21) Appl. No.: 14/810,559

(22) Filed: Jul. 28, 2015

(65) Prior Publication Data
US 2017/0028194 A1    Feb. 2, 2017

(51) Int. Cl.
| | | |
|---|---|---|
| A61N 1/375 | (2006.01) | |
| A61N 1/365 | (2006.01) | |
| A61N 1/05 | (2006.01) | |
| A61N 1/37 | (2006.01) | |
| A61B 5/00 | (2006.01) | |
| A61N 1/368 | (2006.01) | |
| A61N 1/372 | (2006.01) | |
| A61B 5/0456 | (2006.01) | |
| A61B 5/042 | (2006.01) | |

(52) U.S. Cl.
CPC ............ *A61N 1/365* (2013.01); *A61B 5/0456* (2013.01); *A61B 5/686* (2013.01); *A61N 1/057* (2013.01); *A61N 1/368* (2013.01); *A61N 1/3702* (2013.01); *A61N 1/3756* (2013.01); *A61N 1/37205* (2013.01); *A61B 5/0422* (2013.01); *A61N 1/056* (2013.01)

(58) Field of Classification Search
None
See application file for complete search history.

(56) References Cited

U.S. PATENT DOCUMENTS

| | | | |
|---|---|---|---|
| 5,507,782 A | | 4/1996 | Kieval et al. |
| 5,571,159 A | * | 11/1996 | Alt ................... A61N 1/0563 607/122 |
| 5,843,132 A | * | 12/1998 | Ilvento ............... A61N 1/056 607/10 |
| 6,181,967 B1 | * | 1/2001 | Alt ....................... A61N 1/39 607/5 |

(Continued)

OTHER PUBLICATIONS

(PCT/US2016/038453) PCT Notification of Transmittal of the International Search Report and the Written Opinion of the International Searching Authority, dated Sep. 16, 2016, 13 pages.

*Primary Examiner* — Erica S Lee (57) ABSTRACT

An implantable medical device having a housing that encloses a pulse generator and a sensing module includes a housing-based cathode electrode electrically coupled to the pulse generator and to the sensing module. A sensing extension extending from the housing proximal end includes an anode electrode electrically coupled to the sensing module for sensing cardiac electrical signals. The sensing extension includes a flotation member that causes the sensing extension to extend away from the housing along a direction of flowing blood when the implantable medical device is deployed within a cardiovascular system of a patient.

21 Claims, 9 Drawing Sheets

(56) References Cited

U.S. PATENT DOCUMENTS

| | | |
|---|---|---|
| 8,204,595 B2 | 6/2012 | Pianca et al. |
| 8,433,409 B2 | 4/2013 | Johnson et al. |
| 8,532,785 B1 | 9/2013 | Crutchfield et al. |
| 8,541,131 B2 | 9/2013 | Lund et al. |
| 8,634,912 B2 | 1/2014 | Bornzin et al. |
| 8,634,919 B1 * | 1/2014 | Hou ................. A61N 1/3756 607/122 |
| 8,670,842 B1 | 3/2014 | Bornzin et al. |
| 8,700,181 B2 * | 4/2014 | Bornzin ............ A61N 1/3756 607/119 |
| 2003/0009197 A1 * | 1/2003 | Helland ............. A61N 1/368 607/9 |
| 2004/0147973 A1 | 7/2004 | Hauser |
| 2004/0215139 A1 | 10/2004 | Cohen |
| 2006/0089693 A1 | 4/2006 | Lovett et al. |
| 2006/0259084 A1 * | 11/2006 | Zhang ............... A61N 1/368 607/9 |
| 2009/0030331 A1 * | 1/2009 | Hochareon ......... A61B 5/0215 600/508 |
| 2009/0082828 A1 | 3/2009 | Ostroff |
| 2011/0130822 A1 * | 6/2011 | Cottone ................ A61F 2/91 623/1.15 |
| 2012/0172892 A1 | 7/2012 | Grubac et al. |
| 2013/0023975 A1 * | 1/2013 | Locsin ............... A61N 1/0563 607/122 |
| 2013/0035748 A1 | 2/2013 | Bonner et al. |
| 2013/0110219 A1 | 5/2013 | Bornzin et al. |
| 2013/0116529 A1 | 5/2013 | Min et al. |
| 2013/0116741 A1 | 5/2013 | Bornzin et al. |
| 2014/0107723 A1 | 4/2014 | Hou et al. |
| 2014/0180306 A1 | 6/2014 | Grubac et al. |
| 2015/0165199 A1 | 6/2015 | Karst et al. |
| 2016/0015968 A1 | 1/2016 | Bonner et al. |

* cited by examiner

INTRACARDIAC PACEMAKER WITH SENSING EXTENSION IN PULMONARY ARTERY

TECHNICAL FIELD

The disclosure relates to an implantable intracardiac medical device for delivering cardiac pacing and/or sensing cardiac signals.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular pacing may adequately address some patient conditions, other conditions may require atrial and ventricular pacing, commonly referred to as a dual chamber pacing, in order to maintain a regular heart rhythm.

SUMMARY

In general, the disclosure is directed to an intracardiac pacemaker capable of dual chamber sensing for providing atrial-synchronized ventricular pacing therapy to a patient. In one example, the disclosure provides an implantable medical device including a housing having a proximal end and a distal end and enclosing a pulse generator and a sensing module. The housing may carry a housing-based cathode electrode electrically coupled to the pulse generator and to the sensing module. The implantable medical device further includes a sensing extension extending from the housing proximal end that carries an anode electrode electrically coupled to the sensing module for sensing cardiac electrical signals. The sensing extension further includes a flotation member that causes the sensing extension to extend away from the housing along a direction of flowing blood when the implantable medical device is deployed within a cardiovascular system of a patient.

In another example, the disclosure provides a system including an implantable medical device and a delivery tool for deploying the implantable medical device within the cardiovascular system of a patient. The implantable medical device includes a housing having a proximal end and a distal end that encloses a pulse generator and a sensing module for sensing cardiac electrical signals. The housing may include a housing-based cathode electrode electrically coupled to the pulse generator and to the sensing module. The implantable medical device further includes a sensing extension extending from the housing proximal end. The sensing extension includes an anode electrode electrically coupled to the sensing module for sensing cardiac electrical signals and a flotation member. The delivery tool includes a cavity for receiving the housing and a lumen for receiving the sensing extension extending from the housing proximal end. The delivery tool is used to advance the housing distal end to an implant site within the cardiovascular system of a patient and to release the flotation member into flowing blood to cause the sensing extension to extend away from the housing along a direction of the flowing blood.

In another example, the disclosure provides an implantable medical device that includes a housing enclosing control electronics for sensing a cardiac electrical signal and generating electrical stimulation pulses in response to the sensed cardiac electrical signal. The housing has a proximal end and a distal end. The implantable medical device further includes a sensing extension extending from the housing proximal end that includes at least one electrode electrically coupled to the control electronics and a flotation member coupled to the sensing extension that causes the sensing extension to extend away from the housing along a direction of flowing blood when the implantable medical device is deployed within the cardiovascular system of a patient.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

Figure 1:
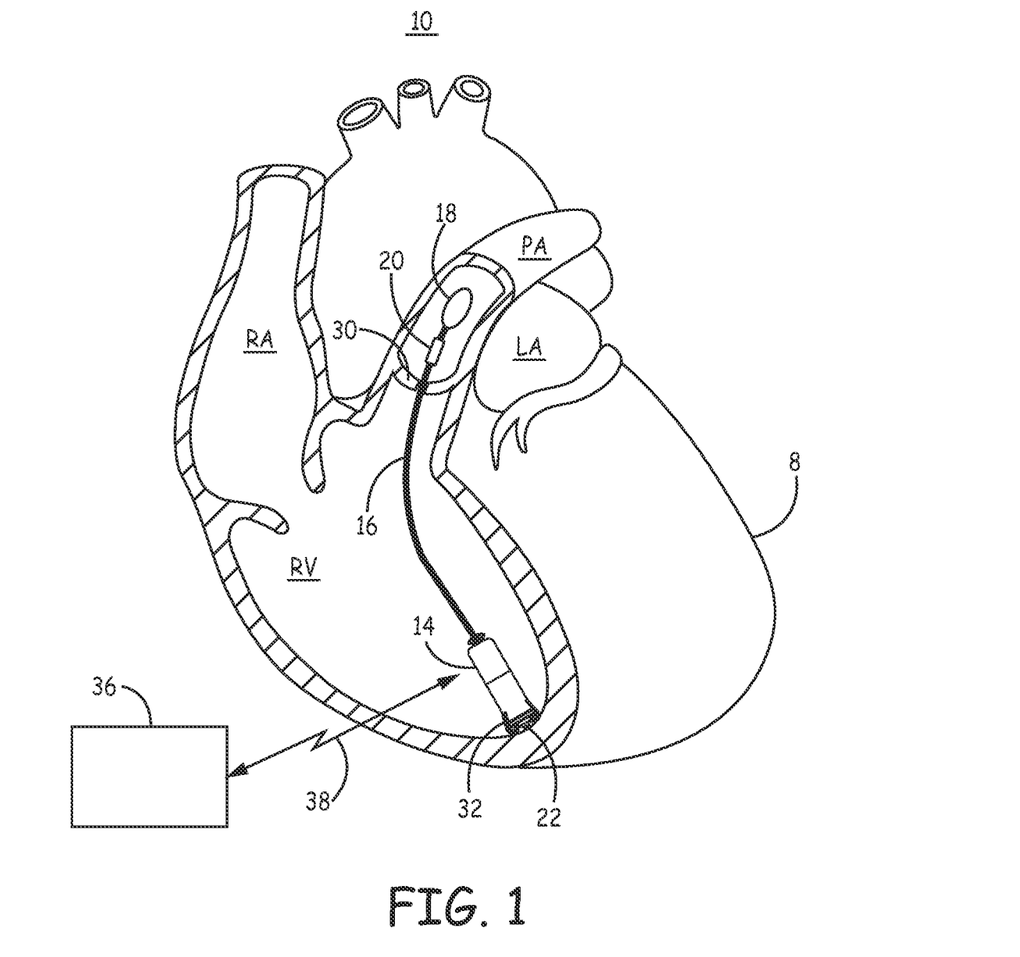
FIG. 1 is a conceptual diagram illustrating an implantable medical device (IMD) that may be used to sense cardiac electrical signals and provide therapy to a patient's heart.

FIG. 1 is a conceptual diagram illustrating an implantable medical device (IMD) 10 that may be used to sense cardiac electrical signals and provide therapy to a patient's heart 8. IMD 10 is an elongated device that includes a housing 14 and a proximal sensing extension 16 extending from housing 14 and carrying at least one sensing electrode 20. The housing 14 encloses electronic circuitry, such as a pulse generator and a sensing module as described below.

IMD 10 is shown deployed in the right ventricle (RV) of a patient's heart 8 with sensing extension 16 extending from the RV into the pulmonary artery (PA). IMD 10 may be delivered transvenously by a catheter advanced into the right atrium (RA) and into the RV. IMD 10 may include a distal fixation member 32, shown as multiple curved tines, for fixing housing 14 at a desired location in the RV, e.g., along the RV apex, upon release from the delivery catheter.

Sensing extension 16 includes a proximal flotation device 18. Upon release from a delivery catheter, the proximal flotation device drifts upstream along the RV outflow tract in to the pulmonary artery (PA). Flotation device 18 is shown as a balloon in FIG. 1 but may alternatively be implemented as an umbrella, sail, kite, or other member that is configured to travel with flowing blood when subjected thereto. When exposed to the flow of blood in the RV, flotation device 18 drifts upstream with blood ejected from the RV into the PA thereby extending sensing extension 16 from the RV into the PA and positioning electrode 20 adjacent the left atrium (LA) for sensing atrial signals.

IMD 10 is configured to deliver ventricular pacing pulses via a distal pacing electrode 22 and return anode electrode 20 carried by sensing extension 16. IMD 10 is configured to sense cardiac electrical signals (including R-waves and P-waves) using the electrodes 22 and 20 positioned in the RV and along the PA, in proximity to LA tissue, respectively. In this way, IMD 10 is enabled to provide dual chamber sensing for controlling ventricular pacing in an atrial synchronized pacing mode, e.g., in a VDD pacing mode.

IMD 10 may be configured for bidirectional wireless telemetry with an external device 36. External device 36 may be a programmer, home monitor, or handheld device. External device 36 may be used to transfer data to and receive data from IMD 10 via a wireless radio frequency (RF) communication link 38 established using BLUETOOTH®, Wi-Fi, Medical Implant Communication Service (MICS) or other RF bandwidth. In some examples, external device 36 may include a programming head that is placed proximate IMD 10 to establish and maintain a communication link, and in other examples external device 36 and IMD 10 may be configured to communicate using a distance telemetry algorithm and circuitry that does not require the use of a programming head and does not require user intervention to maintain a communication link.

Aspects of external device 36 may generally correspond to the external programming/monitoring unit disclosed in U.S. Pat. No. 5,507,782 (Kieval, et al.), hereby incorporated herein by reference in its entirety. External device 36 is often referred to as a "programmer" because it is typically used by a physician, technician, nurse, clinician or other qualified user for programming operating parameters in IMD 10. External device 36 may be located in a clinic, hospital or other medical facility. External device 36 may alternatively be embodied as a home monitor or a handheld device that may be used in a medical facility, in the patient's home, or another location. Operating parameters, such as sensing and therapy delivery control parameters, may be programmed into IMD 10 using external device 36.

Figure 2:
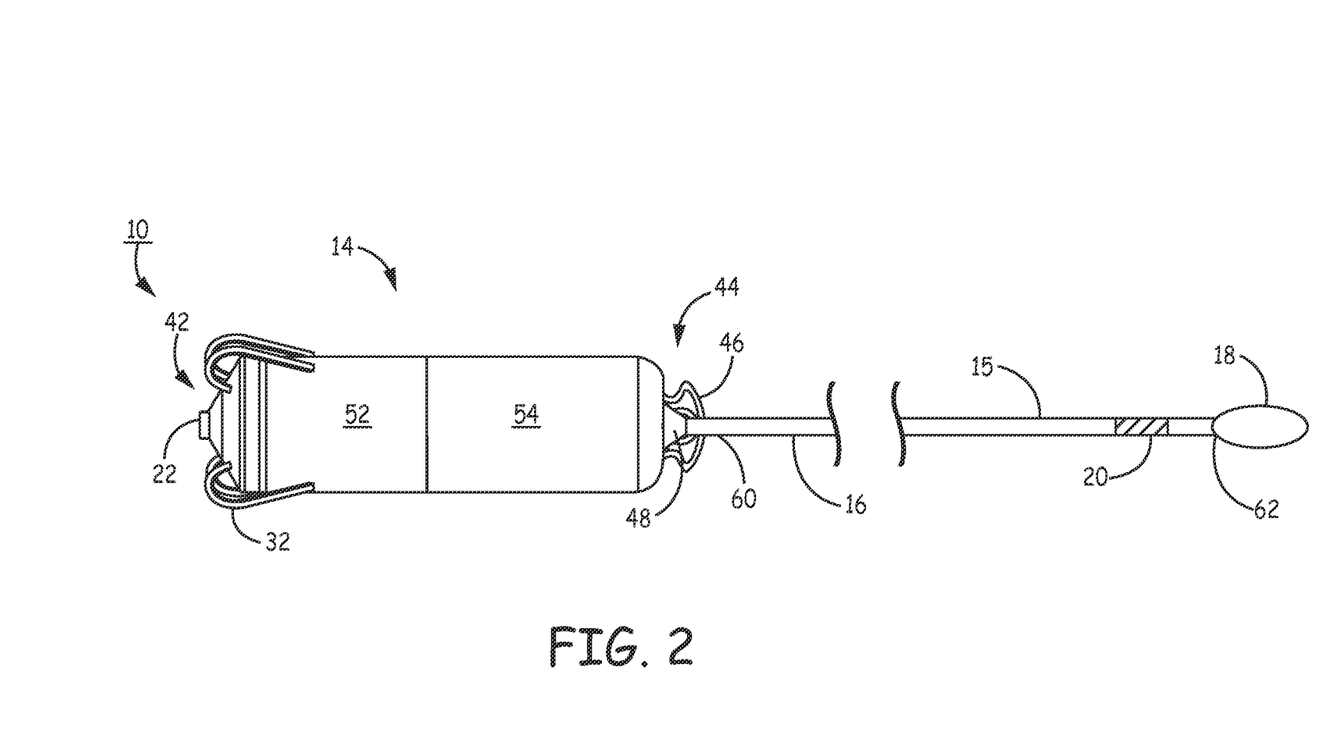
FIG. 2 is a conceptual diagram of the IMD of FIG. 1 according to one embodiment.

FIG. 2 is a conceptual diagram of IMD 10 according to one embodiment. IMD 10 includes housing 14, having a distal end 42 and a proximal end 44, and a proximal sensing extension 16 attached to proximal housing end 44 and extending in a generally proximal direction therefrom. Sensing extension 16 may be non-removably attached to housing 14 via a transition member 48. A distal cathode electrode 22 is carried by housing 14. Sensing extension 16 carries at least one electrode 20 and a proximal flotation member 18.

IMD 10 includes housing-based electrodes 22 for sensing cardiac EGM signals in the RV and delivering ventricular pacing pulses when IMD 10 is implanted in the RV. Electrode 22 is shown as a tip electrode on the housing distal end 42 of IMD 10. Electrode 22 may alternatively be embodied as a ring electrode along a mid-portion of housing 14, for example adjacent housing distal end 42. Distal end 42 is referred to as "distal" in that it is expected to be the leading end as it advanced through a delivery tool, such as a catheter, and placed against a target pacing site.

Electrodes 20 and 22 may be, without limitation, titanium, platinum, iridium or alloys thereof and may include a low polarizing coating, such as titanium nitride, iridium oxide, ruthenium oxide, platinum black among others. Electrodes 20 and 22 form an anode and cathode pair for cardiac pacing and sensing. In alternative embodiments, IMD 10 may include two or more ring electrodes, two tip electrodes, and/or other types of electrodes exposed along housing 14 for delivering electrical stimulation to heart 8. Electrodes 20 and 22 may be positioned at locations along IMD 10 other than the locations shown.

IMD 10 may be deployed by a delivery tool such that proximal sensing extension 16 is released in or becomes drawn into the right ventricular outflow tract (RVOT). Blood flow acting against flotation member 18 will carry the proximal end of sensing extension 16 in the direction of the PA and in some cases across the pulmonary valve. When flotation member 18 "floats" the proximal end of sensing extension 16 into the PA, electrode 20 is in proximity to or adjacent to the LA. The PA courses directly of the LA, specifically over Bachmann's bundle, also known as the interatrial bundle, which is considered the main inter-atrial conduction pathway. A cardiac electrical signal may be sensed between distal electrode 22 and the proximal, extension-based electrode 20. This signal is expected to include higher amplitude P-waves attendant to the atrial depolarization than an intraventricular EGM signal acquired using distal electrode 22 and a second housing-based electrode. By sensing a cardiac electrical signal having a higher P-wave signal strength, IMD 10 is configured to sense P-waves for use in controlling ventricular pacing pulses in an atrial-synchronized ventricular pacing mode.

Sensing extension 16 includes a flexible extension body 15 having a distal end 60 coupled to housing 14 and a free proximal end 62 extending away from housing 14. Extension-based electrode 20 is shown located toward the proximal end 62, spaced distally from flotation member 18, which may be at the terminal proximal end 62. Extension-based electrode 20 may be, with no limitation intended, a few millimeters to a few centimeters distal to flotation member 18. It is recognized that in alternative examples flotation member 18 may be located distally from electrode 20. For example, electrode 20 may be a tip or ring electrode at or adjacent to the proximal end 62 of sensing extension 16 with flotation member 18 located distally from the electrode 20.

Flotation member 18 may have outer dimensions that are advanceable within a delivery tool used to deploy IMD 10 at an implant location without compression of flotation member 18 when retained within a lumen or cavity of the delivery tool. In other examples, flotation member 18 may be a self-expanding member that is held in a compressed position within a delivery tool and expands to a normally expanded position when released from the delivery tool. In other examples, flotation member 18 is an inflatable member that is inflated at the time of manufacture and remains in an inflated state. In still other examples, flotation member is inflated from a compressed position to an expanded position by a user either prior to or after deployment from a delivery tool. Flotation member may be inflated via a self-sealing valve in some examples.

Flotation member 18 may be positively buoyant in blood or is at least neutrally buoyant in blood. As used herein, the terms "at least neutrally buoyant in blood" refers to a buoyancy of the flotation member 18 in blood that is neutral or positively buoyant and is not negatively buoyant in blood. In some examples, the buoyancy of flotation member 18 is selected to promote flotation of the proximal end of sensing extension 16 into the PA that does not create a buoyant force or pulling force due to blood pressure acting on flotation member 18 that is greater than the fixation force of distal fixation member 32. For example, distal fixation member 32 including multiple fixation tines may have a fixation force that is greater than 0.5 Newtons per tine. Flotation member 18 may have a pulling force that is less than 0.5 Newtons when subjected to flowing blood after implantation. For example, the pulling force of flotation member 18 when positioned in flowing blood may be approximately 0.01 N to 0.5 N.

Flotation member 18 may be a compressible or non-compressible hollow member, such as silicone or polyurethane balloon that is filled with air or another lightweight material such as a polyurethane, polyethylene or silicone-based foam. In other examples, flotation member is a compressible or non-compressible solid member molded from a biocompatible material having a density lower than blood. The density of whole blood is approximately 1.06 g/cm$^3$. Flotation member 18 may be molded from a biocompatible polymer, such as polyethylene or polypropylene, having a density less than 1.0 g/cm$^3$ in some examples. Flotation member 18 may include an anti-thrombotic or other coating that reduces the adhesion of cells to flotation member 18 and promotes sliding of blood cells along the surface of flotation member 18. For example, flotation member 18 may have a highly smooth, hydrophilic or neutral surface coating to reduce encapsulation, which may include, with no limitation intended, a hydrogel, polytetrafluoroethylene or GORE-TEX® membrane material.

In some examples, all or a portion of flotation member 18 and other examples of flotation members shown and described herein is formed of a bioabsorbable material, e.g., polylactic acid (PLA), polyglycolic acid (PGA), PLA/PGA copolymers, or polycaprolactone (PCL). Flotation member 18 may be provided to hold sensing extension in an extended position in flowing blood acutely after implantation, but over a period of time, e.g., weeks or months, tissue encapsulation of electrode 20 or any portion of sensing extension 16 may maintain adequate stability of the position of electrode 20 along the PA. Flotation member 18 may be absorbed entirely or partially.

Housing 14 is formed from a biocompatible material, such as a stainless steel or titanium alloy. In some examples, the housing 14 may include an insulating coating. The entirety of the housing 14 may be insulated, but only electrode 22 uninsulated. Examples of insulating coatings include parylene, urethane, PEEK, or polyimide among others. In other examples, an insulating coating of housing 14 is not provided, but electrode 22 is electrically isolated from the remainder of housing 14.

The housing 14 includes a control electronics subassembly 52, which encloses electronic circuitry for sensing cardiac signals, producing pacing pulses and controlling therapy delivery and other functions of IMD 10. Distal cathode electrode 22, shown as a tip electrode, may be coupled via a feedthrough to circuitry within control electronics subassembly 52, e.g., to a pacing pulse generator and electrical signal sensing module. Electrode 20 serves as a return anode that may be paired with distal cathode electrode 22 during pacing and for sensing ventricular EGM signals when IMD 10 is positioned in the RV as shown in FIG. 1. Sensing extension-based electrode 20 is electrically coupled to housing 14 and when paired with distal electrode 22 is used to sense an EGM signal that includes higher amplitude P-waves than an EGM signal sensed using distal cathode electrode 22 paired with another housing-based electrode resulting in a smaller inter-electrode spacing and greater distance from the return anode to atrial tissue.

Housing 14 further includes a battery subassembly 54, which provides power to the control electronics subassembly 52. Battery subassembly 54 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

IMD 10 includes a set of distal fixation tines 32 to secure housing distal end 42 to patient tissue, e.g., by actively engaging with the ventricular endocardium and/or interacting with the ventricular trabeculae. Fixation tines 32 are configured to anchor IMD 10 to position electrode 22 in operative proximity to a targeted tissue for delivering therapeutic electrical stimulation pulses. Numerous types of active and/or passive fixation members may be employed for anchoring or stabilizing IMD 10 in an implant position. IMD 10 may include a set of fixation tines as disclosed in commonly-assigned, pre-grant publication U.S. 2012/0172892 (Grubac, et al.), hereby incorporated herein by reference in its entirety. When properly deployed at a targeted pacing site, fixation tines 32 have a fixation force that is greater than the opposing force against flotation member 18 caused by blood flow in the RVOT that maintains the position of proximal extension end 62 in the PA.

IMD 10 may optionally include a delivery tool interface 46. Delivery tool interface 46 may be located at the proximal end 44 of IMD 10 and is configured to connect to a delivery device, such as a catheter, used to position IMD 10 at an implant location during an implantation procedure, for example within a heart chamber.

A reduced size of housing 14 of IMD 10 enables implantation wholly within a patient's heart such that housing 14 fixed in one heart chamber, e.g., the RV. The length of sensing extension 16 enables extension proximal end 62 to extend into the PA when housing distal end 42 is fixed at a target site. For example, with no limitation intended, housing 14 may have a length between housing distal end 42 and housing proximal end 44 in the range of and including approximately 1 to 5 cm. Sensing extension 16 may a length between extension distal end 60 and extension proximal end 62 of approximately 3 to 15 cm when "floated" near the pulmonary valve (either before or after the pulmonary valve) and more generally may be on the order of approximately 2 cm to 15 cm in length, depending on the overall length of housing 14, distance of targeted pacing site in RV, heart size, and other considerations. The overall length of IMD 10 from housing distal end 42 to sensing extension proximal end 62 is selected to enable implantation of housing 14 wholly in one heart chamber, e.g., the RV, with sensing extension 16, extending toward or adjacent to another heart chamber, e.g., within the PA adjacent the LA.

Figure 3A:
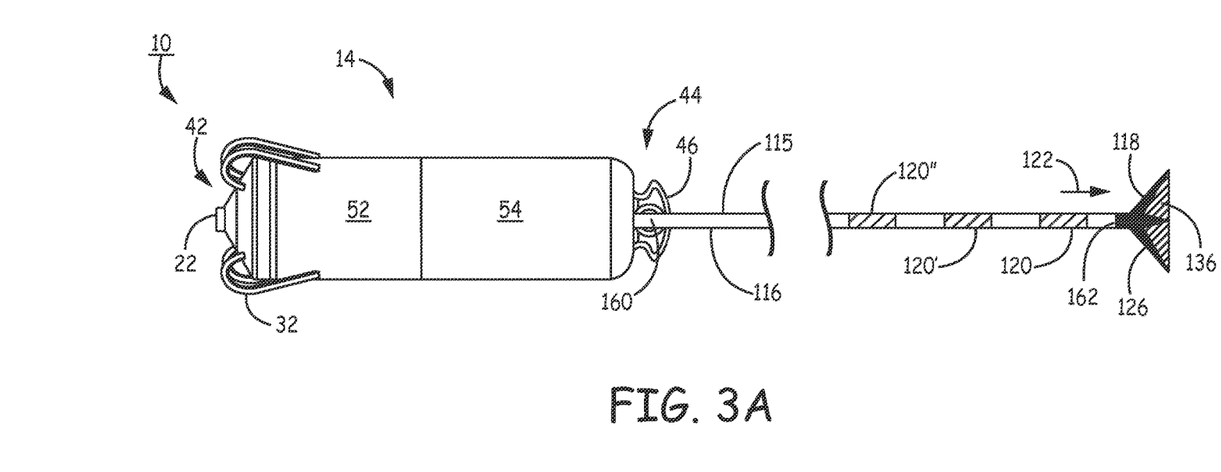
FIG. 3A is a conceptual diagram of an alternative embodiment of the IMD of FIG. 1.

FIG. 3A is a conceptual diagram of an alternative embodiment of IMD 10. In this example, IMD 10 includes a sensing extension 116 extending from housing proximal end 44 that terminates in a flotation member 118 implemented as an umbrella or tent-like structure. Flotation member 118 is pushed in a proximal direction away from housing 14 as indicated arrow 122 by the pressure of flowing blood acting against the distal surface area 126 of flotation member 118. Flotation member 118 has a distal surface area 126 that results in blood pressure against distal surface area 126 that moves extension proximal end 162 into the PA and maintains a substantially extended position of sensing extension 116 such that extension-based electrode 120 is held adjacent or proximate to the LA due to blood pressure acting against distal surface area 126.

In FIG. 3A, sensing extension 116 is shown to include multiple extension-based electrodes 120, 120' and 120". Multiple electrodes may be provided to enable selection of the extension-based electrode 120, 120' or 120" that provides the highest P-wave signal strength and/or least signal noise. Three electrodes 120, 120' and 120" are shown in FIG. 3A, but more than three or less than three electrodes may be carried by sensing extension 116 in various examples. Each electrode carried by sensing extension 116 is coupled to an electrical conductor extending through extension body 115 from the respective to electrode to the sensing extension distal end 160 and may be electrically coupled to housing 14 without requiring an electrical feedthrough crossing housing 14.

Figure 3B:
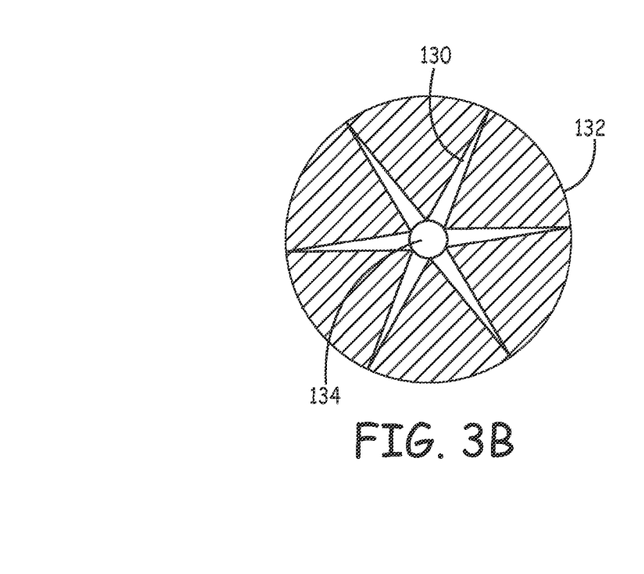
FIG. 3B is an end view of the flotation member of the IMD of FIG. 3A.

FIG. 3B is an end view of flotation member 118. Flotation member 118 may be radially symmetric about a center support 134 that is coaxial with the central axis of sensing extension body 115. Multiple struts 130 extend radially from the center support 134 and a membrane 132 extends between the struts 130 to define a continuous distal surface 126 against which flowing blood acts to push flotation member 118 toward the PA. Struts 130 are shown in FIG. 3A to extend in a slightly proximal direction, i.e., at an obtuse angle from center support 134 and sensing extension body 115. In other examples, struts 130 may extend at other angles, including acute angles or a right angle. When struts 130 extend at an acute angle relative to sensing extension body 115, the orientation of the tent or umbrella like structure is inverted compared to the orientation shown in FIG. 3A.

The proximal face 136 (FIG. 3A) of flotation member 118 may be concave in some examples. Struts 130 may be flexible such that flotation member may be compressed inward when held within a delivery tool. In other examples, struts 130 are relatively rigid such that the shape of flotation member 118 is retained within the delivery tool and after deployment in a heart chamber. While flotation member 118 is described as being a tent-like or umbrella like structure such that proximal surface 136 is a concave surface in the orientation shown (or distal surface 126 is a concave surface in an inverted orientation), a solid cone shaped or pyramidal shape is contemplated that would have a substantially flat proximal surface 136 (or distal surface 126 when inverted relative to the orientation shown).

Flotation member 118 may be formed as a single molded piece that is permanently coupled to sensing extension proximal end 162 or may be formed in two or more steps where struts 130 are formed and membrane 132 is added in a second step. While six struts 130 are shown having equal length, two or more struts may be used and in some examples, the struts 130 may have differing lengths such that flotation member 118 is asymmetric about center support 134. An asymmetric flotation member 118 may cause sensing extension to be pushed in a direction toward the inner wall of the PA rather than toward the center. When pushed toward the wall of the PA, the proximal electrode 120 may be positioned in closer proximity to atrial tissue and may be held in a more stable position as blood flows past flotation member 118.

Figure 3C:
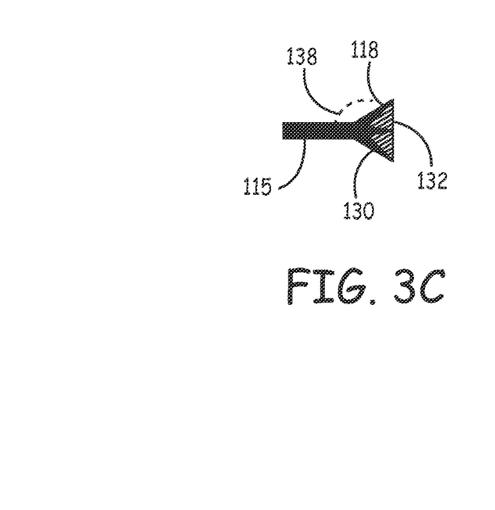
FIG. 3C is a side view of the flotation member of FIG. 3A in a compressed state.

FIG. 3C is a diagram of flotation member 118 in a compressed position. Struts 130 and membrane 132 may be flexible so that when IMD 10 is positioned within an implant delivery tool, flotation member 118 is moved to a compressed position that self-expands to the normal, uncompressed position shown in FIG. 3A when released from the delivery tool. As described below, in conjunction with FIGS. 5-7, sensing extension 116 may extend within a lumen of a delivery tool. When sensing extension 116 extends within a delivery tool lumen, flotation member 118 may be held in the compressed position shown in FIG. 3C. Struts 130 may be pressed inward, toward a central axis of sensing extension body 115, and membrane 132 may fold or become slack in the compressed position such that an outer diameter of flotation member 118 is reduced for advancement along the delivery tool lumen.

In other examples, the position of flotation member 188 shown in FIG. 3C may represent an expanded position of the flotation member 118 rather than a compressed position. The angle 138 between struts 130 and extension body 115 may be relatively more obtuse than the angle shown in FIG. 3A when flotation member 118 is in a normal, self-expanded position. A relatively small surface area 126 exposed to the high velocity blood flow along the RVOT may be sufficient to push flotation member 118 into the PA.

Figure 4A:
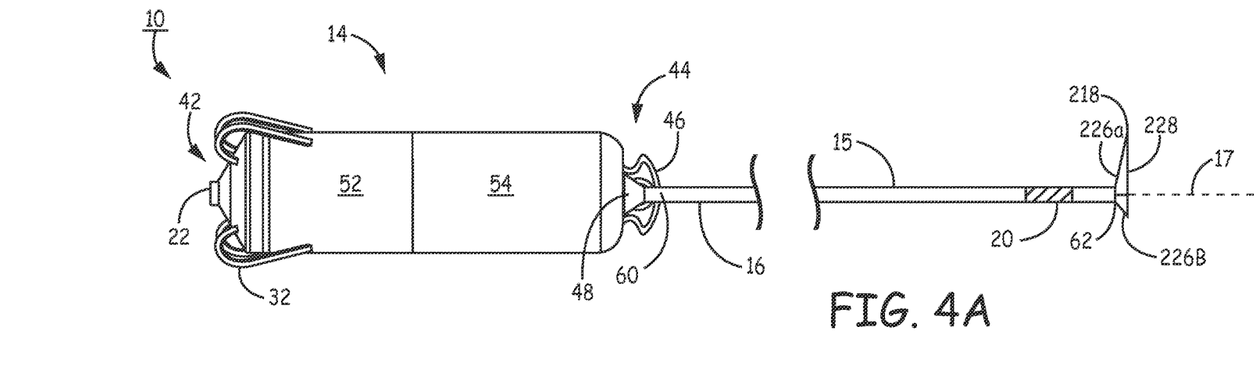
FIGS. 4A through 4C are conceptual diagrams of a flotation member according to other examples.
Figure 4B:
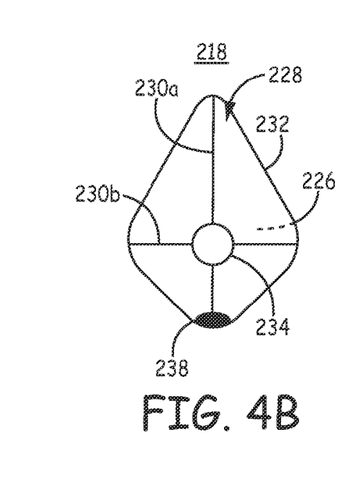

FIG. 4A is a conceptual diagram of IMD 10 according to another example in which sensing extension 16 terminates with a sail or kite-shaped flotation member 218. FIG. 4B is a proximal end view of flotation member 218. Flotation member 218 is asymmetric relative to a center support 234 that is coaxial with the central axis 17 of sensing extension body 15. Flotation member 218 may include perpendicular struts 230a and 230b, collectively 230, extending radially outward from center support 234. A membrane 232 extending between struts 230a and 230b defines a distal surface area 226 against which flowing blood applies a pressure that urges flotation member 218 away from housing 14, extending proximal anode electrode 20 away from housing 14, e.g., into the PA.

Distal surface area 226 is asymmetrical including a larger surface area 226a (FIG. 4A) extending in one direction from center support 234 and a relatively smaller surface area 226b extending in an opposite direction from center support 234. A larger force will be applied by flowing blood against the larger surface area 226a resulting in a non-uniform pushing force relative to the central axis 17 of sensing extension body 15. When released into flowing blood, flotation member 218 may drift toward the pulmonary artery inner wall when the pressure of flowing blood acts to produce a larger total force on the larger distal surface area 226, urging proximal electrode 20 toward atrial tissue. As the proximity of electrode 20 to atrial tissue increases (as electrode 20 gets closer to atrial tissue), P-wave signal strength in the cardiac electrical signal may improve providing more reliable P-wave sensing by IDM 14 for properly triggering atrial-synchronized ventricular pacing pulses.

As shown in FIG. 4B, flotation member 218 may include a weighting member 238 positioned along the smaller surface area 226a, e.g., along an outer edge of membrane 232 or strut 230, to create unequal weighting of flotation member 218 with respect to central axis 17. Weighting member 238 may be a cylinder, bar, sphere, strip or other object that increases the weight of flotation member 218 along the minor or smaller surface area 226b relative to the weight of flotation member 218 along the major or larger surface area 226a so that flotation member 218 is preferentially driven toward the PA vessel wall. Weighting member 238 may be a biocompatible metal, e.g., stainless steel or titanium alloys, which may be adhesively bonded to membrane 232 or overmolded during the formation of membrane 232.

A symmetrically weighted flotation member having a symmetric geometry may oscillate with the cardiac cycle when it remains in the central fluid path of the PA. The blood flow dynamics may drive an asymmetrically weighted flotation member 218 toward the vessel wall, e.g., toward the inferior PA wall near the left atrial roof. The asymmetric geometric shape and/or asymmetrical weighting of flotation member 218 caused by the addition of weighting member 238 may be designed to force the flotation member toward the PA inner wall.

Flotation member 218 may be at least neutrally buoyant in blood even with the addition of weighting member 238. In other examples, weighting member 238 may be slightly negatively buoyant in blood such that the relatively more buoyant major surface area 226a floats "upward" as the weighted minor surface area 226b floats "downward" in the blood flow stream, causing the flotation member 218 to drift toward the PA inner wall. At least a portion of the proximal surface area 228 of flotation member 218 may become pressed along the PA inner wall by the action of blood flowing against the asymmetric distal surface area 226, particularly when weighting member 238 is added. In examples where proximal electrode 20 is spaced proximally from flotation member 218 along sensing extension 16, electrode 20 may be urged against the PA inner wall toward the LA roof.

Additionally, the connection of flotation member 218 to extension body 15 at support member 234 being off-center relative to the flotation member geometry contributes to driving the flotation member 218 toward the PA inner wall. Alternatively, the flotation member may be radially symmetric in geometry, e.g., flotation member 118 of FIG. 4A, and a weighting member 238 may be added along an outer edge of the radially symmetric flotation member to provide asymmetric weighting of the flotation member. A symmetric flotation member having asymmetric weighting may be coupled to extension body 15 coaxially or non-coaxially with central axis 17 of extension body 15.

In various examples, distal surface area 226 may be defined by a membrane 232 that is generally circular or polygonal in shape and supported by one or more struts and in some cases molded as a continuous, self-supporting structure without requiring supporting struts 230. While shown in an asymmetrical position with respect to a central axis 17 of sensing extension body 15, membrane 232 may have a geometry configured to be symmetrical relative to center support 234 and the central axis 17 of sensing extension body 15 in other examples.

Figure 4C:
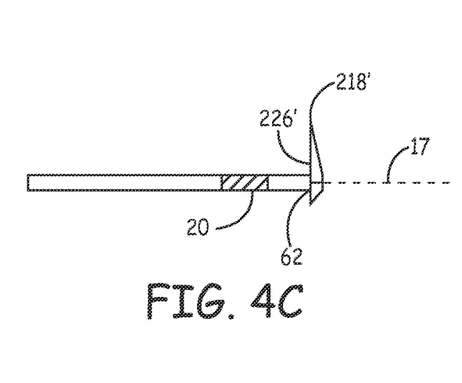

Distal surface area 226 is shown as a generally convex surface, angled in a slightly proximal direction such that blood flowing against distal surface area 226 flows along and past flotation member 218. FIG. 4C is a partial view of IMD 10 according to another example in which sensing extension body 15 is terminated by flotation member 218' having an orientation that is inverted proximally to distally such that distal surface area 226' is a generally concave surface. Flowing blood is received within a concavity defined by distal surface area 226'. The asymmetrical configuration of flotation member 218' may urge sensing extension 16 to bend or curve toward an inner wall of the PA, urging electrode 20 in closer proximity to atrial tissue.

Figure 4D:
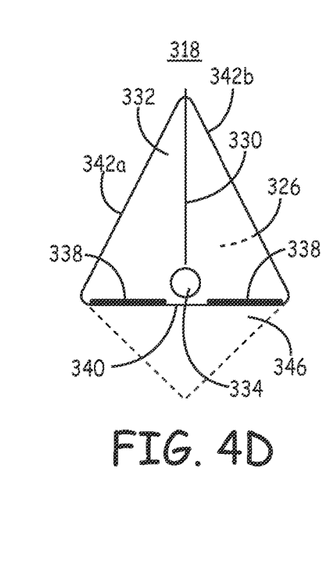
FIG. 4D is a proximal end view of another example of a flotation member.

FIG. 4D is a proximal end view of another example of a flotation member 318. In this example, flotation member is generally triangular, with the support member 334 which provides a connection point to sensing extension body 16 adjacent to or along a minor side 340. A membrane 332 having major sides 342a and 342b and minor side 340 may be self-supporting or supported by strut 330. Membrane 33s defines distal surface area 326 against which flowing blood acts to push flotation member 318 into the PA and toward the PA inner wall. The asymmetry of flotation member 318 with respect to the connection point to extension body 15 at support member 334 causes the flowing blood to urge flotation member 318 (and proximal sensing electrode 20) toward the PA inner wall. Weighting members 338 may be included along minor side 340 to further enhance the preferential flotation of flotation member 318 toward the PA inner wall rather than along a central fluid path of the PA.

In some examples, flotation member 318 may include a bioabsorbable portion 346 that defines a portion of the distal surface area 326 at the time of implantation. The bioabsorbable portion 346 may promote flotation of flotation member 318 into the PA along the RVOT at the time of implantation but may then be absorbed into the blood stream leaving the radially asymmetric flotation member 318 with weighting members 338. The remaining, non-bioabsorbable portion of flotation member 318, as defined by major sides 342a and 342b and minor side 340, is both radially asymmetric in shape and asymmetrically weighted to promote flotation against the PA inner wall after the flotation member 318 has been displaced into the PA and the bioabsorbable portion 346 has absorbed.

The shape (before and after a bioabsorbable portion is absorbed, when included) symmetry, orientation, weighting, surface properties, and connection point to sensing extension body 15 of the various examples of flotation members 18, 118, 218 and 318 of FIGS. 2 through 4D may be selected based upon the particular flow dynamics expected to be encountered at an implant site to promote flotation of sensing extension 16 and proximal electrode 20 to a desired location and to minimize blood flow patterns that might lead to thrombogenesis.

Figure 5:
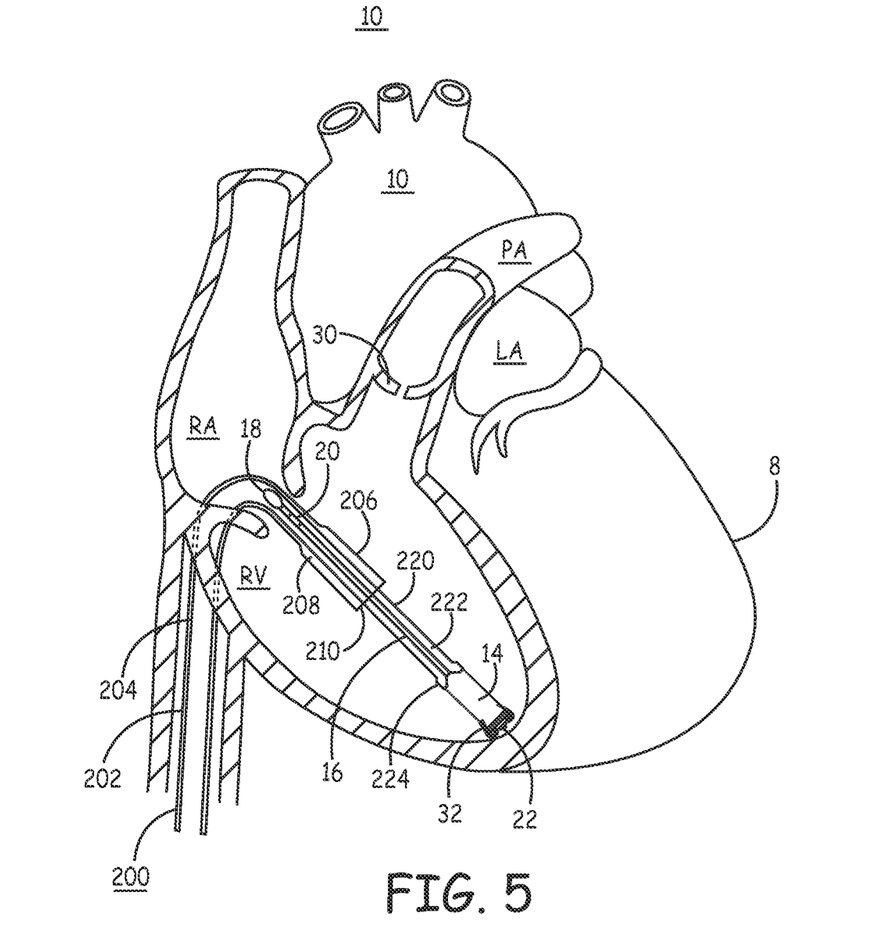
FIGS. 5, 6 and 7 are conceptual diagrams of a delivery tool and the IMD of FIG. 1 as it is deployed into a patient's heart.

FIG. 5 is a conceptual diagram of a delivery tool 200 and IMD 10 as it is deployed into the RV. Delivery tool 200 may include an outer catheter 202 defining an outer lumen 204 through which an inner catheter 220 extends. Inner catheter 220 defines an inner lumen 222 in which proximal sensing extension 16 extends. Prior to deployment of IMD 10, housing 14 may be retained within a delivery tool capsule 206 that defines a cavity 208 for retaining housing 14 during advancement of outer catheter 202 into the RV. Inner catheter 220 may be fully withdrawn into outer lumen 204 such that housing 14 is retained within capsule 208.

With housing 14 retained within capsule 208, delivery tool 200 may be advanced transvenously into the RA, e.g., via the inferior vena cava in the example shown, and advanced further into the RV. Once within the RV or in proximity of a target pacing site, inner catheter 220 may be advanced distally out a distal opening 210 of delivery tool 200 and/or outer catheter 202 may be withdrawn proximally relative to inner lumen 220. Inner catheter 220 may include a distal cone or cup 224 configured to interface with the proximal end 44 of housing 14 for advancing housing distal end 42 out distal opening 210 and against a target pacing site. Fixation member 32 is deployed as housing 14 is released from capsule 206. In some examples, the distal opening 210 is placed adjacent a target pacing site. Fixation member 32 may be held in an extended position within capsule 206. Inner catheter 220 is advanced as outer catheter 202 is retracted such that distal tips of tines included in fixation member 32 pierce into the ventricular endocardial tissue or engage the ventricular reticulum then regain a relaxed position as shown.

Figure 6:
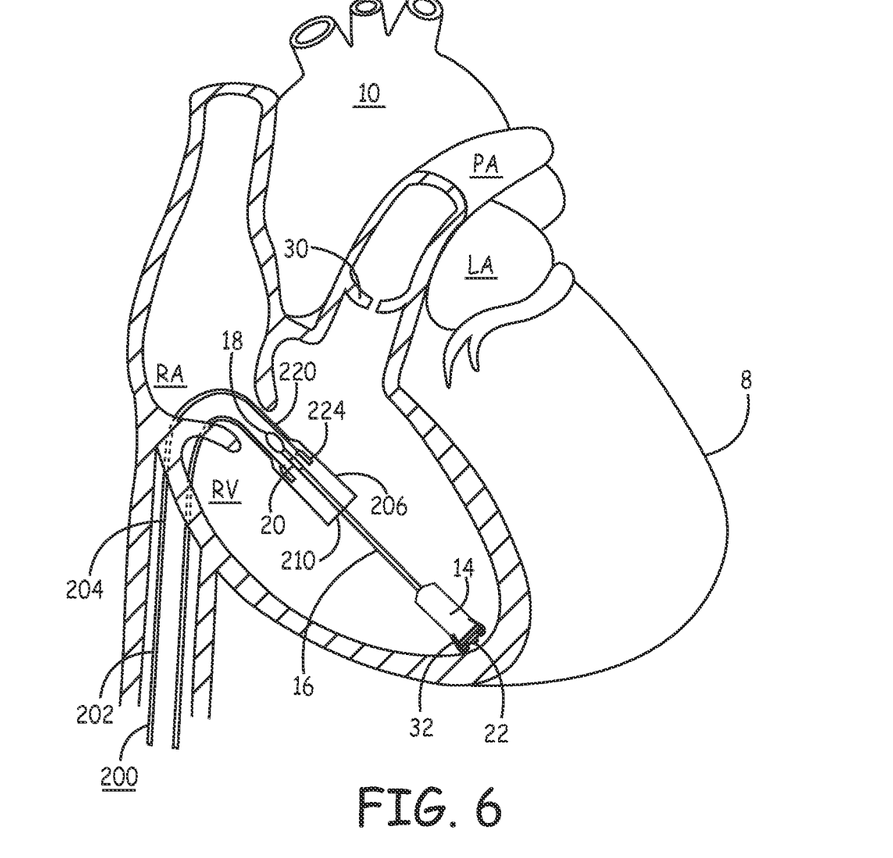
Figure 7:
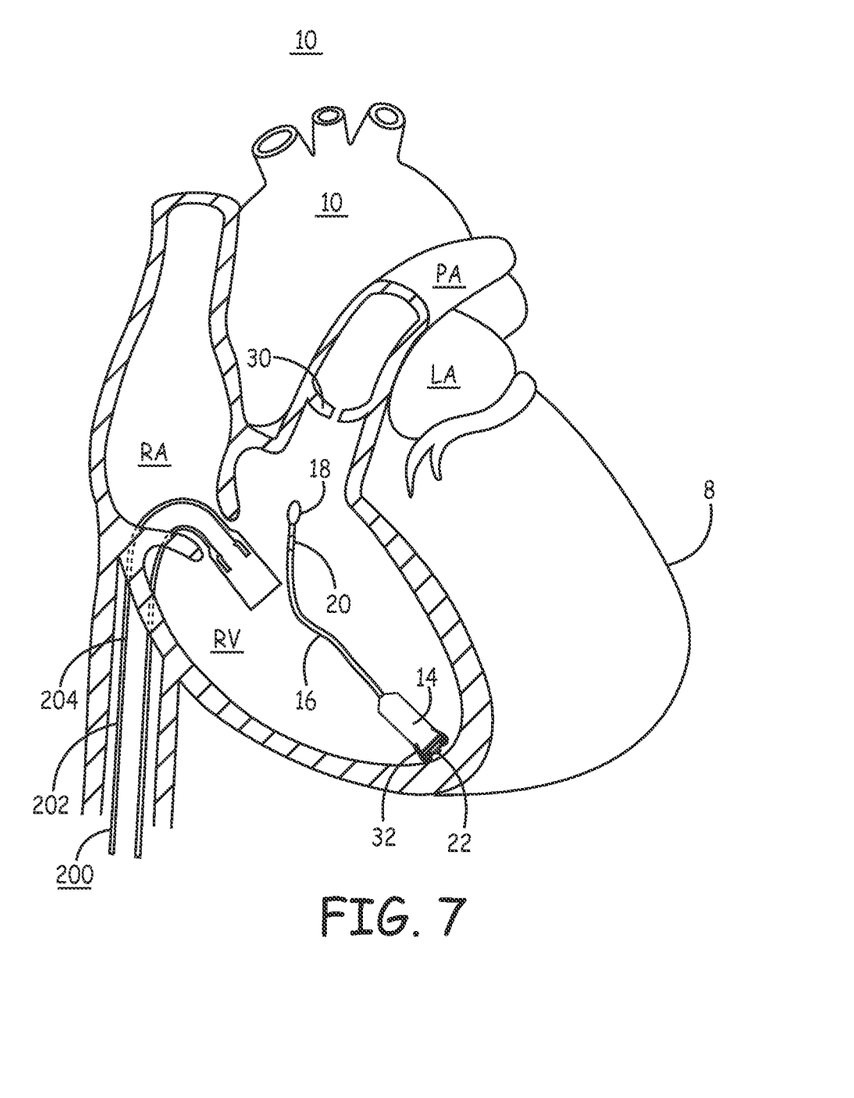

FIG. 6 depicts IMD 10 after inner catheter 220 has been retracted back into outer catheter 202. Distal cup 224 of inner catheter 220 is retracted back into capsule 206 of outer catheter 202. A portion of proximal sensing extension 16 extends within delivery tool 200 such that delivery tool 200 may be advanced as needed to position proximal sensing extension within the RV. Delivery tool 200 is retracted to fully release IMD 10 from delivery tool distal opening 210 such that proximal sensing extension 16 is released from delivery tool 200 as shown in FIG. 7. Flotation member 18 will be released into the RV blood pool and enter the RVOT as the blood flow pattern in the RV acts on flotation member 18.

Flotation member 18 caught in the blood flow pattern of the RV will enter the RVOT and be pushed into the PA by the pressure of blood acting on the flotation member 18 thereby positioning extension-based electrode 20 proximate to or adjacent to the LA, e.g., as shown in FIG. 1. The fixation of housing 14 by fixation member 32 counteract the blood pressure acting on flotation member 18 to maintain distal electrode 22 at the target pacing site while flotation member 18 maintains extension-based proximal electrode 20 in the PA proximate to the LA.

Figure 8:
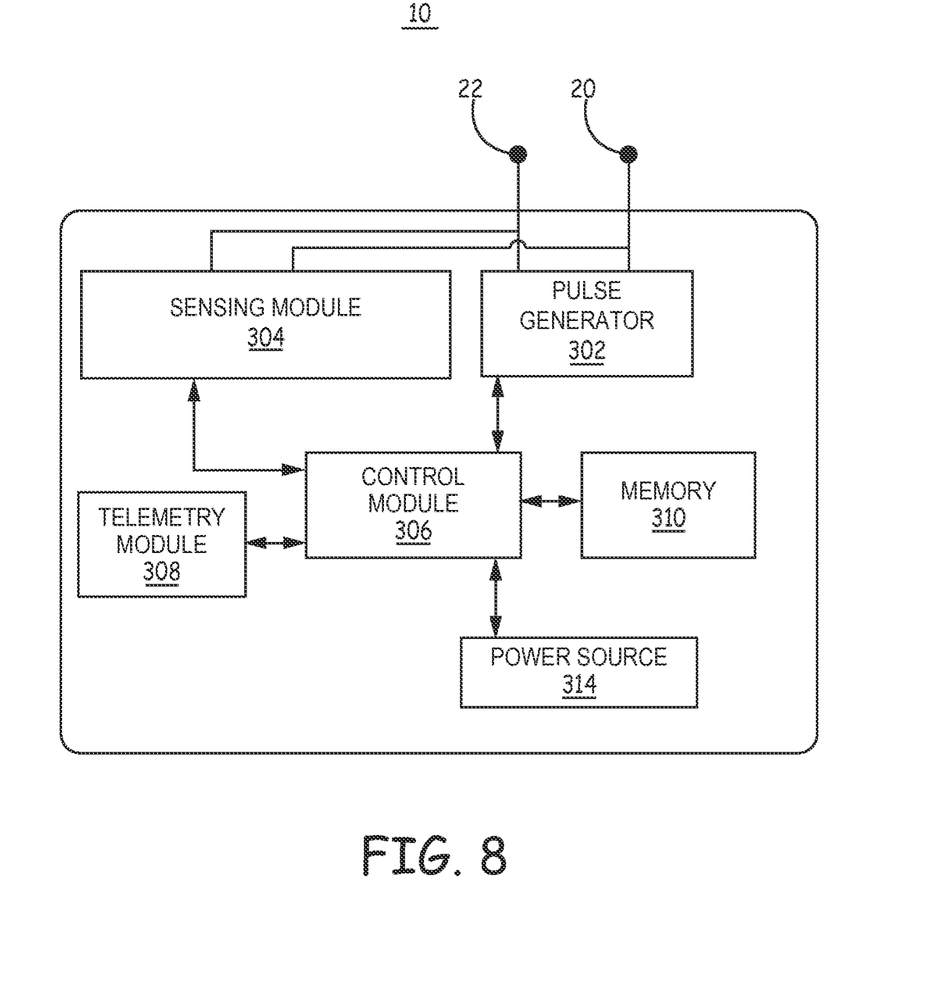
FIG. 8 is a block diagram of the IMD of FIG. 1 according to one example.

FIG. 8 is a block diagram of IMD 10 according to one example. IMD 10 includes a pulse generator 302, a sensing module 304, a control module 306, memory 310, telemetry module 308 and a power source 314. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by IDM 10 may be implemented in control module 306 executing instructions stored in associated memory 310 and relying on input from sensing module 304.

The functional operation of IMD 10 as disclosed herein should not be construed as reflective of a specific form of software or hardware necessary to practice the methods described. It is believed that the particular form of software, hardware and/or firmware will be determined primarily by the particular system architecture employed in the IMD 10 and by the particular sensing and therapy delivery methodologies employed by the IMD 10. Providing software, hardware, and/or firmware to accomplish the described functionality in the context of any modern pacemaker system, given the disclosure herein, is within the abilities of one of skill in the art.

Pulse generator 302 generates electrical stimulation pulses that are delivered to heart tissue via electrodes 20 and 22. Cathode electrode 22 is coupled to pulse generator 302 via an electrically insulated feedthrough crossing housing 14 and return anode electrode 20 may be electrically coupled to housing 14. Pulse generator 302 may include one or more capacitors and a charging circuit to charge the capacitor(s) to a programmed pacing pulse voltage. At appropriate times, as controlled by a pace timing and control module included in control module 306, the capacitor is coupled to cathode electrode 22 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in IMD 10 for charging a pacing capacitor to a predetermined pacing pulse amplitude under the control of control module 306 and delivering a pacing pulse.

Control module 306 controls pulse generator 302 to deliver a pacing pulse in response to expiration of a pacing escape interval according to programmed therapy control parameters stored in memory 310. A pace timing and control module included in control module 306 includes an escape interval timer or counter that is set to various pacing escape intervals used for controlling the timing of pacing pulses relative to a paced or sensed event. Upon expiration of a pacing escape interval, a pacing pulse is delivered. If a cardiac event is sensed during the pacing escape interval by sensing module 304, the scheduled pacing pulse may be inhibited or triggered, and the pacing escape interval may be reset to a new time interval.

Sensing module 304 is configured to receive cardiac electrical signals developed across electrodes 20 and 22. A cardiac event may be sensed by sensing module 304 when the cardiac electrical signal crosses a sensing threshold of a cardiac event detector included in sensing module 304, such as a sense amplifier. The sensing threshold may be an auto-adjusting sensing threshold that may be initially set based on the amplitude of a sensed event and decays at a predetermined decay rate thereafter. In response to a sensing threshold crossing, sensing module 304 passes a sensed event signal to control module 306.

Sensing module 304 may produce P-wave sense event signals that are passed to control module 306 when the cardiac electrical signal crosses a P-wave sensing threshold and R-wave sense event signals when the cardiac electrical signal crosses an R-wave sensing threshold. A P-wave sense event signal may be used by control module 306 to set an atrioventricular (AV) pacing interval. If the AV pacing interval expires without receiving an R-wave sense event signal, control module 306 controls pulse generator 302 to deliver a ventricular pacing pulse synchronized to the sensed P-wave by the AV pacing escape interval.

Memory 310 may include computer-readable instructions that, when executed by control module 306 and/or sensing module 304, cause control module 306 and/or sensing module 304 to perform various functions attributed throughout this disclosure to IMD 10. The computer-readable instructions may be encoded within memory 310. Memory 310 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 310 stores timing intervals, counters, or other data used by control module 306 to control the delivery of pacing pulses by pulse generator 302, e.g., by setting a pacing escape interval timer included in control module 306, according to the techniques disclosed herein.

Power source 314 provides power to each of the other modules and components of IMD 10 as required. Control module 306 may execute power control operations to control when various components or modules are powered to perform various pacemaker functions. Power source 314 may include one or more energy storage devices, such as one or more rechargeable or non-rechargeable batteries. The connections between power source 314 and other pacemaker modules and components are not shown in FIG. 8 for the sake of clarity.

Telemetry module 308 includes a transceiver and associated antenna for transferring and receiving data via a radio frequency (RF) communication link. Telemetry module 308 may be capable of bi-directional communication with an external device 36 as described in conjunction with FIG. 1.

Figure 9:
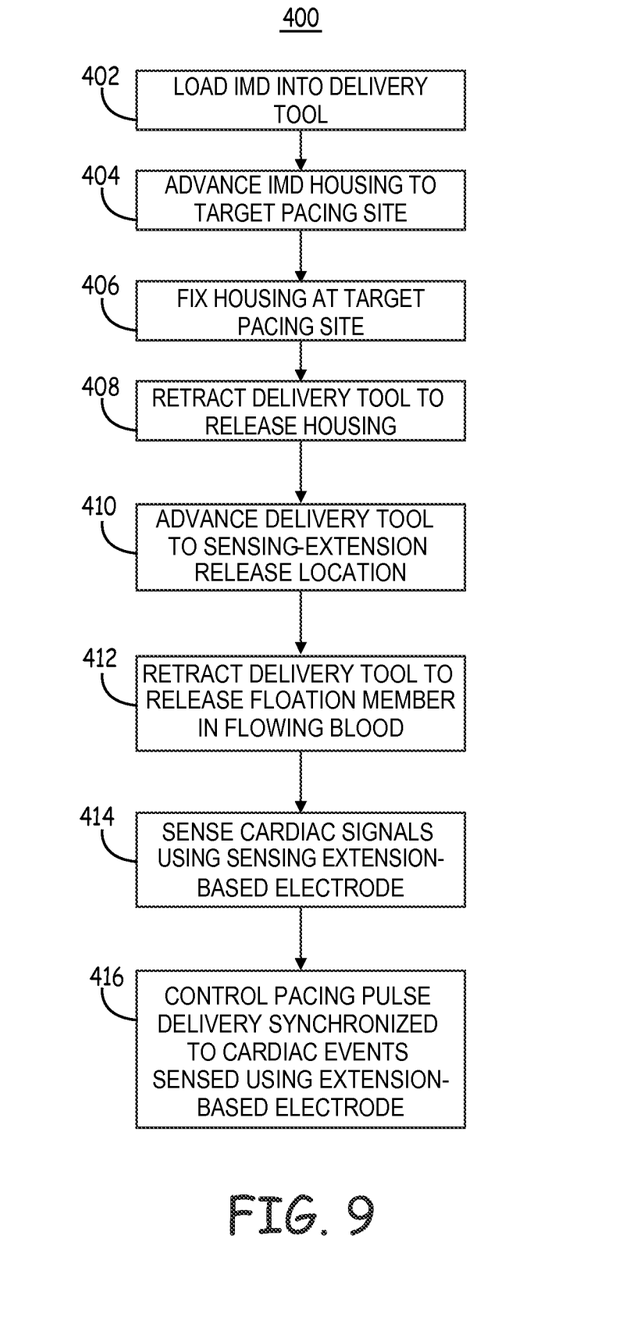
FIG. 9 is a flow chart of a method for deploying the IMD of FIG. 1 for sensing cardiac electrical signals and delivering ventricular pacing pulses synchronized to atrial P-waves.

FIG. 9 is a flow chart 400 of a method for deploying IMD 10 for sensing cardiac electrical signals and delivering ventricular pacing pulses synchronized to atrial P-waves. At block 402, IMD 10 is loaded into a delivery tool including a lumen for receiving proximal sensing extension 16 and a capsule for receiving and retaining the IMD housing 14. The delivery tool is advanced to a target pacing site at block 404 that is the implant site of the IMD housing 14. At block 406, the IMD housing 14 is fixed at the target pacing site, e.g., by advancing IMD housing 14 out a distal opening of the delivery tool to cause the distal fixation member 32 to engage tissue at the target pacing site as described above in conjunction with FIG. 5.

With the IMD housing 14 fixed at the target pacing site, the delivery tool may be retracted to fully release IMD housing 14 from the delivery tool. The proximal sensing extension 16 may remain at least partially within the delivery tool lumen such that the delivery tool may be used to position the sensing extension 16 at a desired release site in flowing blood, e.g., within the RV or along the RVOT as described above in conjunction with FIG. 6. The delivery tool may be fully retracted to release the sensing extension flotation member at block 412. At this point, the IMD 10 may be fully released from the delivery tool. The flotation member 18 released into the flowing blood is subjected to blood pressure that moves the flotation member 18 away from the housing 14 such that the sensing extension extends away from housing 14 and positions at least one extension-based sensing electrode at a desired cardiovascular location away from housing 14 and proximate to or adjacent to a desired cardiac electrical signal sensing site.

At block 414, the sensing extension-based electrode 20 that is "floated" away from housing 14 is used with a housing-based electrode, e.g., cathode 22, for sensing cardiac electrical signals. The control module of IMD 10 controls pacing pulse delivery at the target pacing site using the housing-based distal cathode electrode 22 at block 416. The pacing pulses may be delivered in synchrony with cardiac events sensed using the sensing extension-based electrode 20. For example, the housing-based distal cathode electrode 22 may be anchored at an RV pacing site by distal fixation member 32 at block 406 and used to deliver RV pacing pulses at block 416 synchronized to atrial P-waves detected by sensing a cardiac electrical signal at block 414 using extension-based electrode 20 that is positioned along the PA by the action of blood flow and pressure acting on flotation member 18 released in or near the RVOT at block 412.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

For example, the following Items are illustrative of further embodiments:

Item 1. An implantable medical device, comprising:
　a housing having a proximal end and a distal end;
　a pulse generator enclosed by the housing;
　a sensing module enclosed by the housing for sensing cardiac electrical signals;
　a housing-based cathode electrode electrically coupled to the pulse generator and to the sensing module;
　a sensing extension extending from the housing proximal end and comprising:
　　an anode electrode electrically coupled to the sensing module for sensing cardiac electrical signals in a sensing vector comprising the housing-based cathode electrode; and
　　a flotation member that causes the sensing extension to extend away from the housing along a direction of flowing blood when the implantable medical device is deployed within a cardiovascular system of a patient.

Item 2. The device of item 1, wherein the flotation member is a self-expanding member.

Item 3. The device of any one of items 1-2, wherein the flotation member is at least neutrally buoyant in blood.

Item 4. The device of any one of items 1-3, wherein:
　the sensing extension comprises an elongated body extending from a sensing extension proximal end to a sensing extension distal end that is coupled to the housing proximal end;
　the flotation member having a distal surface area coupled to the sensing extension proximal end, against which pressure of the flowing blood acts to extend the anode electrode away from the housing.

Item 5. The device of any one of items 1-4, wherein the flotation member comprises at least one of a membrane that is radially asymmetric about a central axis of the sensing extension and a weighting member that causes the flotation member to be asymmetrically weighted with respect to a central axis of the sensing extension.

Item 6. The device of any one of items 1-5, further comprising a fixation member coupled to the housing distal end configured to anchor the housing at an implant site, wherein the fixation member has a fixation force greater than a pulling force caused by blood flowing against the flotation member when the housing is anchored at the implant site.

Item 7. The device of any one of items 1-6, wherein the flotation member has a distal surface area against which the flowing blood acts that is asymmetric with a central axis of the sensing extension.

Item 8. The device of any one of items 1-7, wherein the flotation member comprises a supporting member and a membrane extending from the supporting member that defines a distal surface area against which the flowing blood acts.

Item 9. The device of any one of items 1-8, wherein the sensing extension comprises an elongated body extending from a sensing extension proximal end to a sensing extension distal end that is coupled to the housing;

the sensing extension having an overall length from sensing extension proximal end to the sensing extension distal end that reaches a pulmonary artery of the patient when the flotation member extends away from the housing along a right ventricular outflow tract when the housing distal end is implanted in a right ventricle of the patient.

Item 10. The device of any one of items 1-9, wherein the flotation member comprises a bioabsorbable material.

Item 11. A system, comprising:
an implantable medical device comprising:
a housing having a proximal end and a distal end;
a pulse generator enclosed by the housing;
a sensing module enclosed by the housing;
a housing-based cathode electrode electrically coupled to the pulse generator and to the sensing module;
a sensing extension extending from the housing proximal end and comprising:
an anode electrode electrically coupled to the sensing module for sensing cardiac electrical signals in a sensing vector comprising the housing-based cathode electrode, and
a flotation member; and
a delivery tool comprising a cavity for receiving the housing and a lumen for receiving the sensing extension extending from the housing proximal end for advancing the housing distal end to an implant site within a cardiovascular system of a patient and releasing the flotation member into flowing blood to cause the sensing extension to extend away from the housing along a direction of the flowing blood.

Item 12. The system of item 11, wherein the flotation member is a self-expanding member.

Item 13. The system of any one of items 11-12, wherein the flotation member is at least neutrally buoyant in blood.

Item 14. The system of any one of items 11-13, wherein:
the sensing extension comprises an elongated body extending from a sensing extension proximal end to a sensing extension distal end that is coupled to the housing proximal end;
the flotation member having a distal surface area against which pressure applied by the flowing blood acts to extend the anode electrode away from the housing.

Item 15. The system of any one of items 11-14, wherein the flotation member comprises at least one of a membrane that is radially asymmetric about a central axis of the sensing extension and a weighting member that causes the flotation member to be asymmetrically weighted with respect to a central axis of the sensing extension.

Item 16. The system of any one of items 11-15, further comprising a fixation member coupled to the housing distal end configured to anchor the housing at the implant site, wherein the fixation member has a fixation force greater than a pulling force caused by blood flowing against the flotation member when the housing is anchored at the implant site.

Item 17. The system of any one of items 11-16, wherein the flotation member has a distal surface area against which the flowing blood acts that is asymmetric with a central axis of the sensing extension.

Item 18. The system of any one of items 11-17, wherein the flotation member comprises a supporting member and a membrane extending from the supporting member that defines a distal surface area against which the flowing blood acts.

Item 19. The system of any one of items 11-18, wherein the sensing extension comprises an elongated body extending from a sensing extension proximal end to a sensing extension distal end that is coupled to the housing;
the sensing extension having an overall length from the sensing extension proximal end to the sensing extension distal end that reaches a pulmonary artery of the patient when the flotation member extends away from the housing along a right ventricular outflow tract when the housing distal end is implanted in a right ventricle of the patient.

Item 20. The system of any one of items 11-19, wherein the flotation member comprises a bioabsorbable material.

Item 21. An implantable medical device, comprising:
a housing enclosing control electronics for sensing a cardiac electrical signal and generating electrical stimulation pulses in response to the sensed cardiac electrical signal, the housing having a proximal end and a distal end;
a sensing extension extending from the housing proximal end and comprising at least one electrode electrically coupled to the control electronics; and
a flotation member coupled to the sensing extension that causes the sensing extension to extend away from the housing along a direction of flowing blood when the implantable medical device is deployed within a cardiovascular system of a patient.

Thus, various examples of an implantable medical device including a sensing extension having a flotation member have been described. It is recognized that various modifications may be made to the described embodiments without departing from the scope of the following claims.

The invention claimed is:

1. An implantable medical device, comprising:
a housing having a proximal end and a distal end;
a pulse generator enclosed by the housing;
a sensing module enclosed by the housing for sensing cardiac electrical signals;
a housing-based cathode electrode electrically coupled to the pulse generator and to the sensing module;
a sensing extension extending from the housing proximal end and comprising:
an anode electrode electrically coupled to the sensing module for sensing cardiac electrical signals in a sensing vector comprising the housing-based cathode electrode; and
a flotation member configured to cause the sensing extension to extend away from the housing along a direction of flowing blood when the implantable medical device is deployed within a cardiovascular system of a patient.

2. The device of claim 1, wherein the flotation member is a self-expanding member.

3. The device of claim 1, wherein the flotation member is at least neutrally buoyant in blood.

4. The device of claim 1, wherein:
the sensing extension comprises an elongated body extending from a sensing extension proximal end to a sensing extension distal end that is coupled to the housing proximal end;
the flotation member having a distal surface area coupled to the sensing extension proximal end, against which pressure of the flowing blood acts to extend the anode electrode away from the housing.

5. The device of claim 1, wherein the flotation member comprises at least one of a membrane that is radially asymmetric about a central axis of the sensing extension and a weighting member that causes the flotation member to be asymmetrically weighted with respect to a central axis of the sensing extension.

6. The device of claim 1, further comprising a fixation member coupled to the housing distal end configured to anchor the housing at an implant site, wherein the fixation member has a fixation force greater than a pulling force caused by blood flowing against the flotation member when the housing is anchored at the implant site.

7. The device of claim 1, wherein the flotation member has a distal surface area against which the flowing blood acts that is asymmetric with a central axis of the sensing extension.

8. The device of claim 1, wherein the flotation member comprises a supporting member and a membrane extending from the supporting member that defines a distal surface area against which the flowing blood acts.

9. The device of claim 1, wherein the sensing extension comprises an elongated body extending from a sensing extension proximal end to a sensing extension distal end that is coupled to the housing;
the sensing extension having an overall length from sensing extension proximal end to the sensing extension distal end that is configured to reach a pulmonary artery of the patient when the flotation member extends away from the housing along a right ventricular outflow tract when the housing distal end is implanted in a right ventricle of the patient.

10. The device of claim 9, further comprising a control module coupled to the sensing module and the pulse generator and configured to:
detect an atrial P-wave from the cardiac electrical signals sensed from the sensing vector comprising the sensing extension anode electrode and the housing-based cathode electrode; and
control the pulse generator to deliver a ventricular pacing pulse synchronized to the detected atrial P-wave using the housing-based cathode electrode.

11. The device of claim 1, wherein the flotation member comprises a bioabsorbable material.

12. A system, comprising:
an implantable medical device comprising:
a housing having a proximal end and a distal end;
a pulse generator enclosed by the housing;
a sensing module enclosed by the housing;
a housing-based cathode electrode electrically coupled to the pulse generator and to the sensing module;
a sensing extension extending from the housing proximal end and comprising:
an anode electrode electrically coupled to the sensing module and configured for sensing cardiac electrical signals in a sensing vector comprising the housing-based cathode electrode, and
a flotation member; and
a delivery tool comprising a cavity for receiving the housing and a lumen for receiving the sensing extension extending from the housing proximal end and configured for advancing the housing distal end to an implant site within a cardiovascular system of a patient and releasing the flotation member into flowing blood to cause the sensing extension to extend away from the housing along a direction of the flowing blood.

13. The system of claim 12, wherein the flotation member is a self-expanding member.

14. The system of claim 12, wherein the flotation member is at least neutrally buoyant in blood.

15. The system of claim 12, wherein:
the sensing extension comprises an elongated body extending from a sensing extension proximal end to a sensing extension distal end that is coupled to the housing proximal end;
the flotation member having a distal surface area against which pressure applied by the flowing blood acts to extend the anode electrode away from the housing.

16. The system of claim 12, wherein the flotation member comprises at least one of a membrane that is radially asymmetric about a central axis of the sensing extension and a weighting member that causes the flotation member to be asymmetrically weighted with respect to a central axis of the sensing extension.

17. The system of claim 12, further comprising a fixation member coupled to the housing distal end configured to anchor the housing at the implant site, wherein the fixation member has a fixation force greater than a pulling force caused by blood flowing against the flotation member when the housing is anchored at the implant site.

18. The system of claim 12, wherein the flotation member has a distal surface area against which the flowing blood acts that is asymmetric with a central axis of the sensing extension.

19. The system of claim 12, wherein the flotation member comprises a supporting member and a membrane extending from the supporting member that defines a distal surface area against which the flowing blood acts.

20. The system of claim 12, wherein the sensing extension comprises an elongated body extending from a sensing extension proximal end to a sensing extension distal end that is coupled to the housing;
the sensing extension having an overall length from the sensing extension proximal end to the sensing extension distal end configured to reach a pulmonary artery of the patient when the flotation member extends away from the housing along a right ventricular outflow tract when the housing distal end is implanted in a right ventricle of the patient.

21. The system of claim 12, wherein the flotation member comprises a bioabsorbable material.

* * * * *